United States Patent
Karim et al.

(12) 
(10) Patent No.: US 6,579,895 B2
(45) Date of Patent: Jun. 17, 2003

(54) USE OF A CELECOXIB COMPOSITION FOR FAST PAIN RELIEF

(75) Inventors: Aziz Karim, Skokie, IL (US); Andrew M. Brugger, Libertyville, IL (US); Ping Gao, Portage, MI (US); Fred Hassan, Peapack, NJ (US); James C. Forbes, Glenview, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/866,165

(22) Filed: May 25, 2001

(65) Prior Publication Data

US 2002/0028238 A1 Mar. 7, 2002

Related U.S. Application Data

(60) Provisional application No. 60/207,729, filed on May 26, 2000.

(51) Int. Cl.[7] ............................................. A61K 31/415
(52) U.S. Cl. ...................... 514/406; 514/263; 514/282; 514/317
(58) Field of Search ........................................ 514/406

(56) References Cited

U.S. PATENT DOCUMENTS

| | | |
|---|---|---|
| 4,826,689 A | 5/1989 | Violanto et al. |
| 5,145,684 A | 9/1992 | Liversidge et al. |
| 5,298,262 A | 3/1994 | Na et al. |
| 5,302,401 A | 4/1994 | Liversidge et al. |
| 5,336,507 A | 8/1994 | Na et al. |
| 5,340,564 A | 8/1994 | Illig et al. |
| 5,346,702 A | 9/1994 | Na et al. |
| 5,352,459 A | 10/1994 | Hollister et al. |
| 5,354,560 A | 10/1994 | Lovrecich |
| 5,384,124 A | 1/1995 | Courteille et al. |
| 5,429,824 A | 7/1995 | June |
| 5,503,723 A | 4/1996 | Ruddy et al. |
| 5,510,118 A | 4/1996 | Bosch et al. |
| 5,518,187 A | 5/1996 | Bruno et al. |
| 5,518,738 A | 5/1996 | Eickhoff et al. |
| 5,534,270 A | 7/1996 | De Castro |
| 5,536,508 A | 7/1996 | Canal et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,622,938 A | 4/1997 | Wong |
| 5,662,883 A | 9/1997 | Bagchi et al. |
| 5,665,331 A | 9/1997 | Bagchi et al. |
| 5,718,919 A | 2/1998 | Ruddy et al. |
| 5,747,001 A | 5/1998 | Wiedmann et al. |
| 5,760,068 A | 6/1998 | Talley et al. |
| 5,892,053 A | 4/1999 | Zhi et al. |

FOREIGN PATENT DOCUMENTS

| | | | |
|---|---|---|---|
| WO | WO 93/25190 A1 | 12/1993 | |
| WO | WO 96/24336 A1 | 8/1996 | |
| WO | WO 97/14407 A1 | 4/1997 | |
| WO | WO 98/35666 A1 | 8/1998 | |
| WO | WO 99/65469 A2 | 12/1999 | |
| WO | WO 00/18374 A1 | 4/2000 | |
| WO | WO 00/30615 A1 | 6/2000 | |
| WO | WO 00/32189 A1 | 6/2000 | ......... A61K/31/415 |
| WO | WO 00/72827 A2 | 12/2000 | ............ A61K/9/16 |
| WO | WO 01/45706 A1 | 6/2001 | .......... A61K/31/42 |

OTHER PUBLICATIONS

Davies, et al., "Clinical Pharmacokinetics and Pharmacodynamics of Celecoxib", Clin. Pharmacokinet. 38:3 pp.225–242, (2000).

Paulson, et al., "Evidence for Polymorphism in the Canine Metabolism of the Cyclooxygenase 2 Inhibotor, Celecoxib", Drug Metab. Dispos. 27:10 ,pp. 1133–1142, (1999).

Paulson, et al., "Metabolism and Excretion of [14C] Celecoxib in Healthy Male Volunteers", Drug Metab. Dispos. 28:3: pp. 308–314, (2000).

*Primary Examiner*—Rebecca Cook
(74) *Attorney, Agent, or Firm*—Harness, Dickey & Pierce (57) ABSTRACT

There is provided a method of rapidly relieving pain in a mammalian, preferably human, subject. The method comprises orally administering to the subject an effective pain-relieving amount of a composition comprising celecoxib formulated in such a way as to provide, when tested in fasting humans in accordance with standard pharmacokinetic practice, a blood plasma concentration profile of celecoxib in which a concentration of about 250 ng/ml is attained not later than about 30 minutes after oral administration.

29 Claims, 4 Drawing Sheets

USE OF A CELECOXIB COMPOSITION FOR FAST PAIN RELIEF

CROSS REFERENCE TO RELATED APPLICATION

This application claims priority to U.S. application Ser. No. 60/207,729 filed May 26, 2000.

FIELD OF THE INVENTION

The present invention relates to new uses of certain orally deliverable pharmaceutical formulations containing the selective cyclooxygenase-2 inhibitory drug celecoxib, for fast relief of pain, and for manufacture of medicaments useful in treatment of pain.

BACKGROUND OF THE INVENTION

Numerous compounds have been reported having therapeutically and/or prophylactically useful selective cyclooxygenase-2 inhibitory effect, and have been disclosed as having utility in treatment or prevention of specific cyclooxygenase-2 mediated disorders or of such disorders in general. Among such compounds are a large number of substituted pyrazolyl benzenesulfonamides as reported in U.S. Pat. No. 5,760,068 to Talley et al., including for example the compound 4-[5-(4-methylphenyl)-3-(trifluoromethyl)-1H-pyrazol-1-yl]benzenesulfonamide, also referred to herein as celecoxib. Celecoxib has the structure shown in formula (I):

(I)

A need for orally deliverable pharmaceutical compositions giving fast relief of pain exists. A particular need exists for such compositions giving fast relief of pain through selective inhibition of cyclooxygenase-2 (COX-2), without the undesirable side effects associated with inhibition of cyclooxygenase-1 (COX-1) that can occur with conventional non-steroidal anti-inflammatory drugs (NSAIDs). An especial need exists for such compositions giving fast relief of pain through selective inhibition of COX-2, yet exhibiting an onset of effective pain relief at least as rapid as standard NSAIDs used in the art, for example ibuprofen.

Celecoxib is well known as a highly effective selective COX-2 inhibitory drug and is widely prescribed for treatment of chronic inflammatory diseases such as rheumatoid arthritis and osteoarthritis. Celecoxib is available under the trademark Celebrex® of Pharmacia Corporation in capsule dosage forms containing 100 mg or 200 mg of the drug. Although these dosage forms can provide very effective relief of pain, they can, at least in some acute pain situations, exhibit a slower onset of pain relief than a standard NSAID such as ibuprofen.

A suspension of particulate celecoxib in a vehicle of apple juice is disclosed in Ecuador Patent Application No. 98-2761 ("EC 98-2761" which corresponds to WO 00/32189, Jun. 8, 2000). See in particular Example 13 therein, which describes preparation of such a suspension by dissolving celecoxib in ethanol containing 5% polysorbate 80 and adding the resulting mixture to apple juice prior to oral administration to 10 healthy male subjects. The dose administered was 300 mg celecoxib. An equal 300 mg dose was administered for comparison, in the form of three 100 mg capsules containing formulated celecoxib having a $D_{90}$ particle size of about 37 $\mu$m (i.e., 90% by weight of celecoxib particles in the formulation were smaller, in their longest dimension, than about 37 $\mu$m). Pharmacokinetic parameters disclosed indicate that the suspension gave a higher $C_{max}$, shorter $T_{max}$ and shorter $T_{1/2}$ than the capsules as indicated in Table 1 below, where $C_{max}$ is the average maximum blood plasma concentration of celecoxib following administration, $T_{max}$ is the average length of time from administration until $C_{max}$ is reached, and $T_{1/2}$ is the average terminal half-life of blood plasma concentration of celecoxib following $T_{max}$.

TABLE 1

Pharmacokinetics of celecoxib suspension and capsule formulations (from Ecuador Patent Application No. 98-2761)

|  | 300 mg celecoxib as suspension | 300 mg celecoxib as capsules |
| --- | --- | --- |
| $C_{max}$ (ng/ml plasma) | 1526.5 | 1076.5 |
| $T_{max}$ (h) | 1.42 | 1.94 |
| $T_{1/2}$ (h) | 11.53 | 15.57 |

Ibuprofen in a typical acute pain relief dose of 400 mg normally provides an adequate level of suppression of pain, for example post-surgical pain, by about 1 hour after administration. Celecoxib in capsule form normally takes longer, for example about 2 hours, to achieve a similar level of pain suppression. No suggestion is made in above-cited EC 98-2761 that the apparently modest reduction in $T_{max}$ exhibited by the disclosed suspension by comparison with the capsule formulation, when administered in a 300 mg dose, could be associated with a major improvement in onset of pain relief, or that the suspension formulation of celecoxib could be at least comparable with ibuprofen in onset of pain relief.

Above-cited EC 98-2761 merely discloses in general terms that compositions of the invention disclosed therein, i.e., including the disclosed capsule formulations as well as the suspension composition of Example 13 thereof, are effective "for pain management generally (particularly post-oral surgery pain, post-general surgery pain, post-orthopedic surgery pain, and acute flares of osteoarthritis)". Nevertheless, this reference contains no suggestion that the suspension composition might provide an effective pain relieving amount of celecoxib nor was it appreciated by this reference that an effective pain-relieving concentration of 250 nm/ml plasma or greater could be achieved in a rapidly bioavailable formulation. This is particularly in view of the extensive binding of celecoxib to plasma albumin which was known to occur following oral administration (Davies et al., Clin. Pharmacokinet. 38:225–242, 2000). Thus, one could not have predicted that a particular plasma concentration would produce analgesia.

Australian Patent Applications No. 200042711, No. 200043730 and No. 200043736 disclose compositions comprising a selective COX-2 inhibitory drug, a $5HT_1$ receptor agonist and caffeine, said to be useful for treating migraine.

Although objectives of the present invention are not limited to any particular measure of analgesic response, a method of providing analgesia with an onset time of 60 minutes or less, especially 30 minutes or less and ideally 15 minutes or less, by oral administration of a celecoxib composition would be an important advance in the art.

SUMMARY OF THE INVENTION

It has now surprisingly been discovered that celecoxib can provide acceptable relief of acute pain within about 60 minutes or less after oral administration, in some cases much less than 60 minutes, for example as little as about 15 to about 45 minutes, after oral administration, if it is formulated and administered in such a way as to give a particular pharmacokinetic profile as defined below.

Accordingly, there is now provided a therapeutic method comprising orally administering to a mammalian, preferably human, subject in need of analgesia an effective pain-relieving amount of a composition comprising celecoxib (herein also referred to as a celecoxib composition) formulated in such a way as to provide, when tested in fasting humans in accordance with standard pharmacokinetic practice, a blood plasma concentration profile of celecoxib in which a concentration of about 250 ng/ml is attained not later than about 30 minutes after oral administration. The plasma concentrations of 250 ng/ml or greater achieved by the compositions and methods of the present invention at or before 30 minutes after oral administration and, more preferably, at or before 15 minutes after oral administration, are effective pain-relieving plasma concentrations.

It has not previously been known that fast absorption of celecoxib, as indicated by such a blood plasma concentration profile, is important in achieving fast onset of analgesic response. As noted above, celecoxib is known to be extensively bound to plasma albumin following oral administration (Davies et al., supra) such that one could not have predicted that a particular plasma concentration would produce analgesia.

There is also provided a method of use of celecoxib, formulated in such a way as to provide, when tested in an effective pain-relieving amount in fasting humans in accordance with standard pharmacokinetic practice, a blood plasma concentration profile of celecoxib in which a concentration of about 250 ng/ml is attained not later than about 30 minutes after oral administration, in preparation of a medicament for rapid relief of pain in a mammalian, preferably human, subject.

The phrase "in need of analgesia" as applied to a subject herein embraces a subject suffering mild to intense pain at the time of administration of the celecoxib composition, as well as a subject that can reasonably be expected to have an imminent onset of mild to intense pain, e.g., within about 1 to about 2 hours and especially within about 30 minutes, if no analgesic is administered. An illustrative example of a situation where a subject can reasonably be expected to have such an imminent onset of pain is a period immediately following surgery under local anesthetic, as effects of the local anesthetic wear off.

What constitutes an effective pain-relieving amount, or dose, of a celecoxib composition according to the invention depends, among other factors, on the body weight of the subject and the intensity of the pain being treated. Normally an effective celecoxib dose will be found in the range of about 1 to about 6 mg/kg body weight. For an average 75 kg subject, this range equates to a celecoxib dose of about 75 to about 450 mg. Proportionately smaller or larger doses can be appropriate for subjects having lesser or greater body weight. Such a dose can be administered as needed, but typically administration 1 to about 4 times per day, in most cases 1 or 2 times a day, provides adequate continuing relief of pain.

An "effective pain-relieving concentration" or "effective pain-relieving plasma concentration" as used herein is intended to mean a plasma level in a patient which when tested in a standardized test involving patient scoring of the severity of pain, achieves a mean score indicating pain relief. In one such test as described hereinbelow, patients score pain on a scale of from 0 (no reduction in severity of pain) to 4 (complete relief of pain) and a mean score equal to or greater than a given value is deemed to constitute effective pain-relief. A mean score of 0.5 or greater and, more preferably, 1.0 or greater in such a test, as exemplified herein, is deemed to constitute effective pain relief. The skilled artisan will appreciate, however, that other approaches can be used to assess the severity of pain and relief from such pain.

Thus, one aspect of the present invention involves a therapeutic method for analgesia in which a composition comprising celecoxib is administered orally to a subject, in a formulation which provides detectable pain relief not later than about 30 minutes after oral administration. By "detectable pain relief", it is meant that the formulation produces effective pain relief which is measurable by a standard method such as described above. For example, a formulation, which achieves a mean score of 0.5 or greater and, more preferably, 1.0 or greater on a scale of from 0 to 4 in a testing system as described above, is deemed to provide detectable pain relief. The invention is not limited to use of any particular type of formulation, so long as it exhibits the pharmacokinetic profile defined herein. Examples of suitable formulation types are described below.

Protocols for conducting human pharmacokinetic studies are well known in the art and any standard protocol can be used to determine whether a particular celecoxib formulation satisfies the pharmacokinetic criteria set out herein. An example of a suitable protocol is described below.

An advantage of the present invention is that relief of pain, even intense pain as can occur, for example, following oral, general or orthopedic surgery, is achieved significantly faster, i.e., in a significantly shorter time after administration, than is achievable with standard formulations of celecoxib.

A further advantage is that, by contrast with pain relief methods involving NSAIDs lacking selectivity for inhibition of COX-2, rapid relief of pain can be obtained without the side-effects commonly associated with COX-1 inhibition. Thus the method of the present invention is especially suitable where NSAIDs are contraindicated, for example in patients with peptic ulcers, gastritis, regional enteritis, ulcerative colitis or diverticulitis, patients with a recurrent history of gastrointestinal lesions, patients with gastrointestinal bleeding, coagulation disorders including anemia such as hypothrombinemia, hemophilia and other bleeding problems, or kidney disease, patients prior to surgery, or patients taking anticoagulants.

Other features and advantages of the invention will be in part apparent and in part pointed out hereinafter.

DETAILED DESCRIPTION OF THE INVENTION

The present invention provides a method of rapidly relieving pain in a mammalian subject, the method comprising orally administering to the subject an effective pain-relieving amount of a composition comprising celecoxib formulated in such a way as to provide, when tested in fasting humans in accordance with standard pharmacokinetic practice, a blood plasma concentration profile of celecoxib in which a concentration of about 250 ng/ml is attained not later than about 30 minutes after oral administration. The plasma concentration of 250 ng/ml achieved by the formulations of the present invention, constitutes an "an effective pain-relieving plasma concentration."

The method of the invention can be used to relieve acute or chronic pain, but is particularly well-suited to acute pain indications such as post-surgical pain or post-traumatic pain. The method of the invention is useful for treatment of non-human mammalian subjects or patients, including domestic, farm and exotic animals, such as for example dogs horses, zoo animals and the like, but is primarily useful for treatment of human subjects or patients.

Celecoxib used in the method of the invention can be prepared by a process known per se, for example by processes described in U.S. Pat. No. 5,466,863 to Talley et al. or in U.S. Pat. No. 5,892,053 to Zhi & Newaz.

A suitable dose of celecoxib, administered according to the method of the invention, is typically in the range of about 1 to about 6 mg/kg body weight, preferably about 1.3 to about 5.3 mg/kg body weight and more preferably about 2 to about 3.5 mg/kg body weight, for example about 2.7 mg/kg body weight. Depending on the body weight of the subject, a suitable dosage amount of celecoxib is typically about 50 to about 400 mg, preferably about 100 to about 300 mg. Surprisingly good results can be obtained with dosage amounts less than 300 mg, such as about 100 to about 275 mg, or about 150 to about 250 mg, for example about 200 mg.

The doses set out above relate to a single administration, and can be repeated as needed. Generally no more than about 4 doses per day will be needed, and in most cases 1 or 2 doses per day will be found sufficient.

A key to the present invention is selecting a formulation that provides a pharmacokinetic profile wherein a threshold blood plasma concentration of celecoxib of at least about 250 ng/ml is attained not later than about 30 minutes after oral administration. This analgesically effective blood concentration is achieved in the present invention by utilizing a composition containing celecoxib in a rapidly bioavailable formulation, i.e. a "fast-acting formulation". The celecoxib is present in the composition at dose levels as discussed above, which are typically used in formulations which do not achieve such plasma concentrations shortly after administration, i.e. within about 30 minutes and, more preferably, within about 15 minutes after oral administration.

In preferred methods, a formulation is selected providing a higher concentration than about 250 ng/ml within about 30 minutes. For example, a formulation can be expected to be particularly effective for relief of pain if a blood plasma concentration of at least about 300 ng/ml, more preferably at least about 400 ng/ml and most preferably at least about 500 ng/ml, is attained within about 30 minutes following oral administration of the formulation. There is no critical upper limit of blood plasma concentration so long as the dosage amounts set out above are not significantly exceeded; however it is likely that no significant incremental benefit will be obtained from blood plasma concentrations of celecoxib greatly in excess of about 500 ng/ml, for example in excess of about 1000 ng/ml, within the first 30 minutes.

Preferably, a threshold blood plasma concentration of celecoxib of about 250 ng/ml is attained not later than about 15 minutes after oral administration of the formulation.

In a particularly preferred embodiment the formulation provides a blood plasma concentration of celecoxib that attains about 300 ng/ml not later than about 30 minutes, most preferably not later than about 15 minutes, after oral administration.

In another particularly preferred embodiment the formulation exhibits a $T_{max}$ not greater than about 1.25 hours, most preferably not greater than about 1 hour.

In yet another particularly preferred embodiment the formulation exhibits, in comparative pharmacokinetic testing versus a standard commercial formulation of celecoxib, such as Celebrex® 200 mg capsules of Pharmacia Corporation, a $T_{max}$ not greater than about 50%, even more preferably not greater than about 33%, and most preferably not greater than about 25%, of the $T_{max}$ exhibited by said standard commercial formulation.

Any standard pharmacokinetic protocol can be used to determine blood plasma concentration profile in humans following oral administration of a celecoxib formulation, and thereby establish whether that formulation meets the pharmacokinetic criteria set out herein.

Illustratively, a randomized single-dose crossover study can be performed using a group of healthy adult human subjects. The number of subjects is sufficient to provide adequate control of variation in a statistical analysis, and is typically about 10 or greater, although for certain purposes a smaller group can suffice. Each subject receives, by oral administration at time zero, a single dose (e.g., 200 mg) of a test formulation of celecoxib, normally at around 8 am following an overnight fast. The subject continues to fast and remains in an upright position for about 4 hours after administration of the celecoxib formulation. Blood samples are collected from each subject before administration (e.g., 15 minutes prior to administration) and at several intervals after administration. For the present purpose it is preferred to take several samples within the first hour, and to sample less frequently thereafter. Illustratively, blood samples can be collected 15, 30, 45, 60 and 90 minutes after administration, then every hour from 2 to 10 hours after administration. Optionally additional blood samples can be taken later, for example 12 and 24 hours after administration. If the same subjects are to be used for study of a second test formulation, a period of at least 7 days is allowed to elapse before administration of the second formulation. Plasma is separated from the blood samples by centrifugation and the separated plasma is analyzed for celecoxib by a validated high performance liquid chromatography (HPLC) procedure with a lower limit of detection of 10 ng/ml (see for example, Paulson et al., *Drug Metab. Dispos.* 27:1133–1142, 1999; Paulson et al., *Drug Metab. Dispos.* 28:308–314, 2000; Davies et al, supra). Plasma concentrations of celecoxib referenced herein are intended to mean total celecoxib concentrations including both free and bound celecoxib as determined upon extraction from the plasma sample and HPLC detection according to methods known in the art such as those identified above.

Any formulation giving the desired pharmacokinetic profile is suitable for administration according to the present method. One exemplary type of formulation giving such a profile has celecoxib ultra-finely dispersed in a liquid medium. If the liquid medium is one in which celecoxib is of very low solubility, for example an aqueous medium such as water or fruit juice, the celecoxib is present as suspended particles. The smaller the particles, the higher is the probability that the formulation will exhibit the presently desired pharmacokinetic profile. The ultimate in particle size reduction is represented by a true solution of celecoxib in a pharmaceutically acceptable solvent such as polyethylene glycol (PEG), e.g., PEG having an average molecular weight of about 400 (PEG-400), or a glycol ether, e.g., diethylene glycol monoethyl ether (DGME).

In a formulation having celecoxib in solid particulate form, it will generally be found necessary for practice of the present invention to provide celecoxib in a particle size range wherein $D_{90}$ is less than about 10 μm, for example about 10 nm to about 10 μm. ($D_{90}$ is a diameter such that 90% by weight of the particles are smaller than this diameter in their longest dimension.) Preferably, $D_{90}$ is less than about 2 μm.

Optionally, the celecoxib is nanoparticulate, i.e., having $D_{90}$ less than about 1 μm. In nanoparticulate celecoxib formulations, weight average particle size is typically about 100 nm to about 800 nm, for example about 150 nm to about 600 nm, or about 200 nm to about 400 nm. Pharmaceutical compositions comprising such nanoparticulate celecoxib formulations are useful in methods of the present invention.

In a related embodiment, pharmaceutical compositions useful herein comprise celecoxib formulations wherein the celecoxib has a $D_{25}$ particle size of about 450 nm to about 1000 nm, and more preferably about 500 nm to about 900 nm, the formulation providing at least a substantially similar $C_{max}$ and/or at most a substantially similar $T_{max}$ by comparison with an otherwise similar formulation having a $D_{25}$ particle size of less than 400 nm, and/or providing a substantially greater $C_{max}$ and/or a substantially shorter $T_{max}$ by comparison with an otherwise similar formulation having a $D_{25}$ particle size larger than 1000 nm. ($D_{25}$ is a diameter such that 25% by weight of the particles are smaller than this diameter in their longest dimension.)

In another related embodiment, pharmaceutical compositions useful herein comprise celecoxib formulations wherein the celecoxib is present in solid particles, about 25% to 100% by weight of which have a particle size of about 450 nm to about 1000 nm, preferably about 500 nm to about 900 nm.

In yet another related embodiment, pharmaceutical compositions useful herein comprise nanoparticulate celecoxib formulations wherein the celecoxib is present in solid particles having a weight average particle size of about 450 nm to about 1000 nm, preferably about 500 nm to about 900 nm, the composition providing at least a substantially similar $C_{max}$ and/or at most a substantially similar $T_{max}$ by comparison with an otherwise similar composition having a weight average particle size of less than 400 nm, and/or providing a substantially greater $C_{max}$ and/or a substantially shorter $T_{max}$ by comparison with an otherwise similar composition having a weight average particle size larger than 1000 nm. For purposes of this description, "weight average particle size" can be considered synonymous with $D_{50}$ particle size.

Numerous processes for preparation of nanoparticulate compositions of therapeutic agents are known. Some of these processes use mechanical means, such as milling, to reduce particle size to a nano range, and others precipitate nano-sized particles from solution. Illustrative processes are disclosed in the patent publications cited below.

U.S. Pat. No. 4,826,689 to Violanto & Fischer.
U.S. Pat. No. 5,145,684 to Liversidge et al.
U.S. Pat. No. 5,298,262 to Na & Rajagopalan.
U.S. Pat. No. 5,302,401 to Liversidge et al.
U.S. Pat. No. 5,336,507 to Na & Rajagopalan.
U.S. Pat. No. 5,340,564 to Illig & Sarpotdar.
U.S. Pat. No. 5,346,702 to Na & Rajagopalan.
U.S. Pat. No. 5,352,459 to Hollister et al.
U.S. Pat. No. 5,354,560 to Lovrecich.
U.S. Pat. No. 5,384,124 to Courteille et al.
U.S. Pat. No. 5,429,824 to June.
U.S. Pat. No. 5,503,723 to Ruddy et al.
U.S. Pat. No. 5,510,118 to Bosch et al.
U.S. Pat. No. 5,518,187 to Bruno et al.
U.S. Pat. No. 5,518,738 to Eickhoff et al.
U.S. Pat. No. 5,534,270 to De Castro.
U.S. Pat. No. 5,536,508 to Canal et al.
U.S. Pat. No. 5,552,160 to Liversidge et al.
U.S. Pat. No. 5,560,931 to Eickhoff et al.
U.S. Pat. No. 5,560,932 to Bagchi et al.
U.S. Pat. No. 5,565,188 to Wong et al.
U.S. Pat. No. 5,569,448 to Wong et al.
U.S. Pat. No. 5,571,536 to Eickhoff et al.
U.S. Pat. No. 5,573,783 to Desieno & Stetsko.
U.S. Pat. No. 5,580,579 to Ruddy et al.
U.S. Pat. No. 5,585,108 to Ruddy et al.
U.S. Pat. No. 5,587,143 to Wong.
U.S. Pat. No. 5,591,456 to Franson et al.
U.S. Pat. No. 5,622,938 to Wong.
U.S. Pat. No. 5,662,883 to Bagchi et al.
U.S. Pat. No. 5,665,331 to Bagchi et al.
U.S. Pat. No. 5,718,919 to Ruddy et al.
U.S. Pat. No. 5,747,001 to Wiedmann et al.
International Patent Publication No. WO 93/25190.
International Patent Publication No. WO 96/24336.
International Patent Publication No. WO 97/14407.
International Patent Publication No. WO 98/35666.
International Patent Publication No. WO 99/65469.
International Patent Publication No. WO 00/18374.

International Patent Publication No. WO 00/27369.

International Patent Publication No. WO 00/30615.

One of ordinary skill in the art will readily adapt the processes therein described to preparation of celecoxib in nanoparticulate form.

One method of providing suspended particulate celecoxib in a particle size range suitable for practice of the present invention involves a first step of dissolving the celecoxib in a suitable solvent such as ethanol. Preferably the amount of solvent used is kept to a minimum, but must be sufficient to fully dissolve the celecoxib. Preferably a suitable amount of a wetting agent such as polysorbate 80 is also added to the solvent; this can be done before or after, preferably before, addition of the celecoxib. Celecoxib can be added to the ethanol as technical drug, i.e., without the presence of excipients, or in the form of a celecoxib formulation comprising one or more excipients such as diluents, e.g., lactose and/or microcrystalline cellulose, disintegrants, e.g., croscarmellose sodium, binding agents, e.g., polyvinylpyrrolidone, wetting agents, e.g., sodium lauryl sulfate, and lubricants, e.g., magnesium stearate.

In a second step, the resulting solution of celecoxib is added to an aqueous liquid and vigorously agitated, for example by stirring. The volume of the aqueous liquid is much greater than the volume of the celecoxib solution. The effect of the second step is to precipitate celecoxib as a fine suspension in the aqueous liquid. The aqueous liquid can be water and can include other ingredients, such as one or more materials selected from sweetening agents, flavoring agents and coloring agents. The aqueous liquid can be a beverage such as a fruit juice, e.g., apple juice, grape juice, cranberry juice, orange juice, etc.

If the resulting suspension is allowed to stand, the celecoxib particles tend to agglomerate and/or increase in size by crystal growth. These processes can occur relatively quickly. It is therefore important that the suspension be administered as soon as possible after preparation, preferably not more than about 15 minutes and most preferably not more than about 5 minutes after preparation. It may also be desirable to add substances which delay, diminish or interfere with the formation of celecoxib crystals.

Finely divided particulate or nanoparticulate celecoxib is not necessarily administered in suspension. It can be administered as a solid dosage form such as a capsule or tablet, provided disintegration of the solid dosage form to release celecoxib into the gastrointestinal fluid occurs rapidly enough to generate the presently desired pharmacokinetic profile. Similarly, a solution of celecoxib can be administered in a capsule, such as a hard or soft capsule having a wall comprising gelatin or hydroxypropylmethylcellulose (HPMC), provided the capsule wall dissolves or disintegrates rapidly enough in gastrointestinal fluid to enable the celecoxib thus released to be absorbed into the bloodstream and generate the presently desired pharmacokinetic profile.

Celecoxib is highly hydrophobic; inclusion in the formulation of a wetting agent can provide wetting of celecoxib particles and can improve absorption. This can also help provide a pharmacokinetic profile consistent with the present invention, even where particle size is not ideal. Any suitable wetting agent can be used. Surfactants, hydrophilic polymers and certain clays can be useful as wetting agents. Non-limiting examples of suitable surfactants include benzalkonium chloride, benzethonium chloride, cetylpyridinium chloride, dioctyl sodium sulfosuccinate, nonoxynol 9, nonoxynol 10, octoxynol 9, poloxamers, polyoxyethylene (8) caprylic/capric mono- and diglycerides (e.g., Labrasol™ of Gattefossé), polyoxyethylene (35) castor oil, polyoxyethylene (20) cetostearyl ether, polyoxyethylene (40) hydrogenated castor oil, polyoxyethylene (10) oleyl ether, polyoxyethylene (40) stearate, polysorbate 20, polysorbate 40, polysorbate 60, polysorbate 80 (e.g., Tween™ 80 of ICI), propylene glycol laurate (e.g., Lauroglycol™ of Gattefossé), sodium lauryl sulfate, sorbitan monolaurate, sorbitan monooleate, sorbitan monopalmitate, sorbitan monostearate, tyloxapol, and mixtures thereof. Presently preferred examples include polysorbate 80 and sodium lauryl sulfate.

Formulations useful in the present invention can be imbibable liquids or unit dosage forms. Unit dosage forms useful in the invention typically contain about 10 mg to about 400 mg of celecoxib, for example, a 10, 20, 37.5, 50, 75, 100, 125, 150, 175, 200, 250, 300, 350 or 400 mg dose of celecoxib. Preferred unit dosage forms contain about 50 mg to about 400 mg of celecoxib. More preferred unit dosage forms contain about 100 mg to about 200 mg of celecoxib.

In an imbibable formulation, celecoxib can be present at any suitable concentration. Preferably the concentration is sufficiently high that the volume of liquid that has to be imbibed is not inconveniently great for the patient. For example, for a 200 mg dose, it is preferable that the concentration of celecoxib in an imbibable solution or suspension be not less than about 0.1% weight/volume, so that the volume of solution or suspension to be imbibed is not greater than about 200 ml.

In a unit dosage form, celecoxib is present at a minimum concentration of about 1%, preferably about 4%, more preferably about 10%, and still more preferably about 20%, by weight. The maximum concentration of celecoxib in a unit dosage form depends, among other factors, on the excipients present in the formulation, but is normally about 90%, preferably about 75% and more preferably about 50%, by weight.

In a particular embodiment of the invention, a first celecoxib formulation providing the pharmacokinetic profile required herein is co-administered with a second celecoxib formulation that generates a different pharmacokinetic profile, specifically one exhibiting slower absorption into the bloodstream and therefore a longer $T_{max}$, and typically a lower $C_{max}$. The combination of fast pain relief provided by the first formulation and longer-lasting pain relief provided by the second formulation can reduce the dose frequency required. Alternatively, the second formulation can contain a selective COX-2 inhibitory drug other than celecoxib.

Preferably where co-administration of a "fast-acting" formulation and a "longer-lasting" formulation is desired, the two formulations are combined within a single composition, for example a dual-release composition.

While methods of the present invention are primarily directed towards treatment of fast onset indications such as pain relief, celecoxib compositions useful in such methods are also contemplated to be useful in treatment and/or prevention of a wide range of conditions and disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, such compositions have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions useful in methods of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Such compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are also useful in treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic diseases, such as retinitis, conjunctivitis, retinopathies, uveitis, ocular photophobia, and of acute injury to the eye tissue.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in patients at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Because of the rapid onset of therapeutic effect that can be exhibited by compositions useful in methods of the invention, these compositions have particular advantages over prior formulations for treatment of acute COX-2 mediated disorders, especially for relief of pain, for example in headache, including sinus headache and migraine.

Celecoxib compositions useful in methods of the present invention can be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis (acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index,* 12th Edition (1996), Therapeutic Category and Biological Activity Index, lists therein headed "Analgesic", "Anti-inflammatory" and "Antipyretic").

Particularly preferred combination therapies comprise use of such a celecoxib composition with an opioid compound, more particularly where the opioid compound is codeine, meperidine, morphine or a derivative thereof.

The compound to be administered in combination with a celecoxib composition useful in methods of the invention can be formulated separately from said composition or co-formulated with said composition. Where a celecoxib composition is co-formulated with a second drug, for example an opioid drug, the second drug can be formulated in immediate-release, rapid-onset, sustained-release or dual-release form.

In an embodiment of the invention, particularly where the COX-2 mediated condition is headache or migraine, the celecoxib composition is administered in combination therapy with a vasomodulator, preferably a xanthine derivative having vasomodulatory effect, more preferably an alkylxanthine compound.

Combination therapies wherein an alkylxanthine compound is co-administered with a celecoxib composition as provided herein are embraced by the present embodiment of the invention whether or not the alkylxanthine is a vasomodulator and whether or not the therapeutic effectiveness of the combination is to any degree attributable to a vasomodulatory effect. The term "alkylxanthine" herein embraces xanthine derivatives having one or more $C_{1-4}$ alkyl, preferably methyl, substituents, and pharmaceutically acceptable salts of such xanthine derivatives. Dimethylxanthines and trimethylxanthines, including caffeine, theobromine and theophylline, are especially preferred. Most preferably, the alkylxanthine compound is caffeine.

The total and relative dosage amounts of the celecoxib composition and of the vasomodulator or alkylxanthine are selected to be therapeutically and/or prophylactically effective for relief of pain associated with the headache or migraine. Suitable dosage amounts will depend on the particular patient and the particular vasomodulator or alkylxanthine selected. For example, in a combination therapy with celecoxib and caffeine, typically the celecoxib will be administered in a daily dosage amount of about 50 mg to about 1000 mg, preferably about 100 mg to about 600 mg, and the caffeine in a daily dosage amount of about 1 mg to about 500 mg, preferably about 10 mg to about 400 mg, more preferably about 20 mg to about 300 mg.

The vasomodulator or alkylxanthine component of the combination therapy can be administered in any suitable dosage form by any suitable route, preferably orally. The vasomodulator or alkylxanthine can optionally be coformulated with the celecoxib composition in a single oral dosage form. Thus a solution or solution/suspension formulation useful in methods of the invention optionally comprises both celecoxib and a vasomodulator or alkylxanthine such as caffeine, in total and relative amounts consistent with the dosage amounts set out hereinabove.

The phrase "in total and relative amounts effective to relieve pain", with respect to amounts of celecoxib and a vasomodulator or alkylxanthine in a composition of the present embodiment, means that these amounts are such that (a) together these components are effective to relieve pain, and (b) each component is or would be capable of contribution to a pain-relieving effect if the other component is or were not present in so great an amount as to obviate such contribution.

EXAMPLES

The following Examples are provided for illustrative purposes only and are not to be interpreted as limiting the scope of the present invention. The Examples will permit better understanding of the invention and better perception of its advantages.

Example 1

A single-center, single-dose, double-blind, placebo controlled, parallel group 24 hour study was conducted in a total of 200 patients experiencing moderate to severe post-dental surgery pain. Patients were in an immediate post-surgical phase following extraction of 2 or more impacted third molars requiring bone removal. Patients were stratified based on baseline pain intensity and allocated randomly to four treatment groups for oral dosing:

1. Celecoxib 200 mg capsule (Celebrex® 200 mg).
2. Ibuprofen 400 mg capsule.
3. Celecoxib 200 mg fine suspension.
4. Placebo.

The celecoxib fine suspension was prepared by dissolving celecoxib in ethanol containing 5% polysorbate 80 and adding the resulting mixture to apple juice. The fine suspension was administered within 5 minutes of preparation.

Assessment of pain relief for each patient, based on interview with the patient, was made on a 0–4 scale at the time of dosing and again 15, 30, 45 and 60 minutes and 1.5, 2, 3, 4, 5, 6, 7, 8, 9, 10, 11, 12 and 24 hours after dosing, or until rescue medication was required. A score of 0 was assigned where the patient reported no reduction in severity of pain, a score of 4 was assigned where the patient reported complete relief of pain, and scores of 1, 2 and 3 were assigned to intermediate degrees of pain relief.

Each patient also recorded the time to onset of analgesia by pressing a first stop-watch at the time a perceptible reduction in severity of pain was first noticed, and a second stop-watch at the time a reduction in severity of pain was considered meaningful by the patient.

Blood samples for pharmacokinetic analysis were taken immediately before dosing and again 15, 30, 45 and 60 minutes and 1.5, 2, 3, 4, 5, 6, 7, 8, 9, 10, 11, 12 and 24 hours after dosing. Plasma was separated from the blood samples by centrifugation and the separated plasma was analyzed for celecoxib by a validated HPLC procedure with a lower limit of detection of 10 ng/ml.

Figure 1:
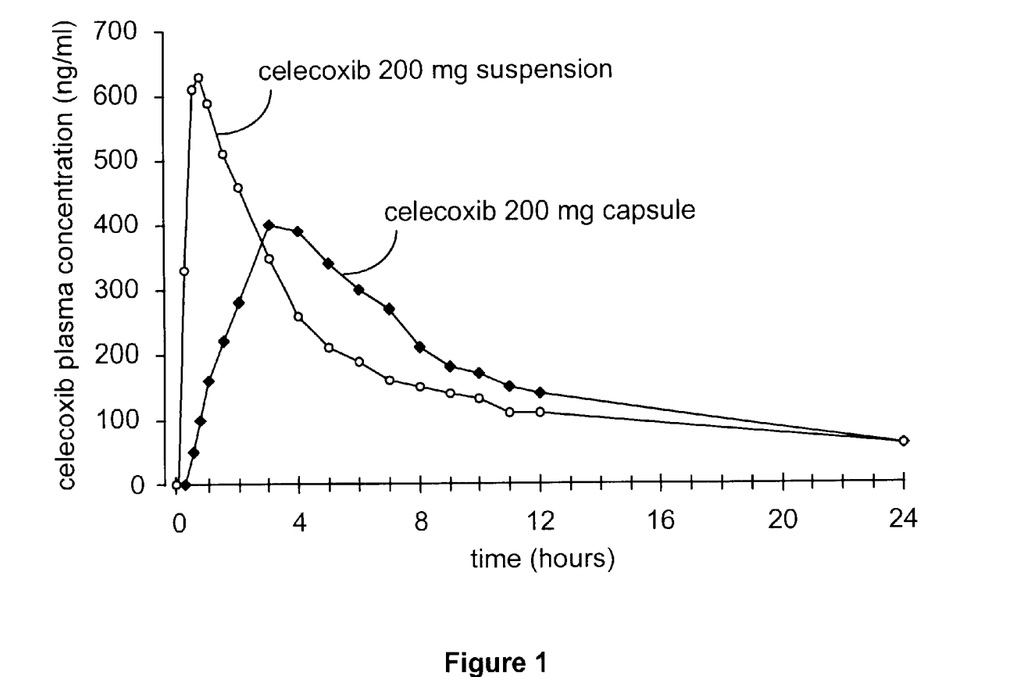
FIG. 1 shows blood plasma concentration profiles of celecoxib administered as a single oral dose of 200 mg, in the form of a capsule (Celebrex® 200 mg, Pharmacia Corporation) or in the form of a fine suspension in apple juice as described in Example 1.

The profile of blood plasma concentration of celecoxib in patients receiving the celecoxib dosage forms is shown for both dosage forms in FIG. 1. It will be noted that with the suspension, a blood plasma concentration greater than 300 ng/ml was attained just 15 minutes after administration, whereas with the commercial capsule it took over 2 hours to reach this concentration. Absorption of celecoxib from the suspension was therefore much faster than from the capsule formulation. Calculated $T_{max}$ for the suspension was 0.88 hours (i.e., about 53 minutes), compared to 3.86 hours for the capsule. $C_{max}$ for the suspension was 703 ng/ml, by comparison with 548 ng/ml for the capsule. Overall bioavailability, as measured by an integral function of blood plasma concentration over 24 hours, i.e., area under the curve, or $AUC_{0-24\ h}$, was similar for the two formulations.

Figure 2:
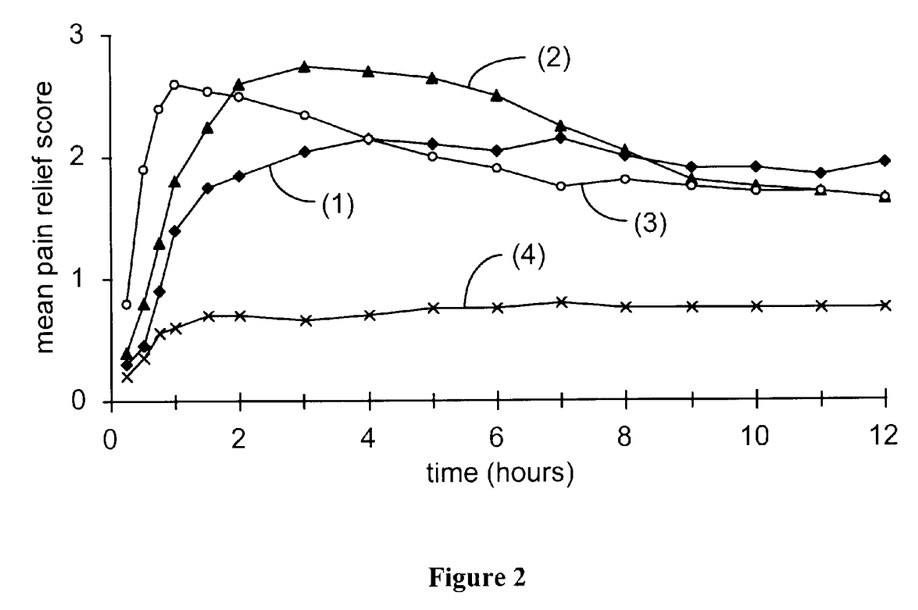
FIG. 2 shows relief of post-surgical pain experienced over a 12-hour period following administration of a single oral dose of (1) 200 mg celecoxib in the form of a capsule (Celebrex® 200 mg, Pharmacia Corporation), (2) 400 mg ibuprofen in the form of a capsule, (3) 200 mg celecoxib in the form of a fine suspension in apple juice as described in Example 1, or (4) placebo.

Average pain relief scores over the 12 hour period following administration of treatments 1–4 are shown in FIG. 2. It will be seen that treatments 1–3 all gave lasting relief of pain by comparison with placebo (treatment 4); indeed pain relief was still evident with treatments 1–3 as much as 24 hours after administration (not shown in FIG. 2).

Figure 3:
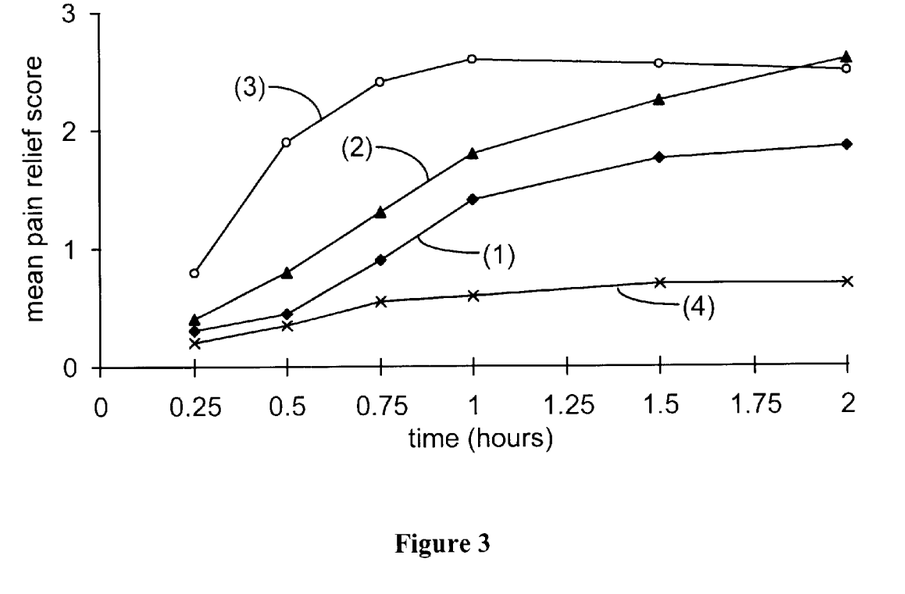
FIG. 3 shows more clearly than FIG. 2 the relief of post-surgical pain experienced in the first 2 hours following administration of the above treatments (1) through (4), to emphasize differences among treatments in time of onset of pain relief.

Progression of pain relief during the first two hours after administration is more clearly seen in FIG. 3. It will be seen that the celecoxib 200 mg suspension (treatment 3) began to show improved pain relief over placebo (treatment 4) as early as 15 minutes after administration. The first clear sign that ibuprofen 400 mg capsule (treatment 2) was giving greater pain relief than placebo was seen 30 minutes after administration, and the first clear sign that celecoxib 200 mg capsule (treatment 1) was giving greater pain relief than placebo was seen 45 minutes after administration.

A mean pain relief score approaching 2 was first seen with celecoxib suspension (treatment 3) at 30 minutes, with ibuprofen capsule (treatment 2) at 1 hour and with celecoxib capsule (treatment 1) at 1.5–2 hours after administration. The pain relief score obtained with celecoxib suspension was statistically significantly superior to that obtained with ibuprofen capsule at all times up to and including 1 hour after administration.

Median time to onset of analgesia as recorded by the patients was 19 minutes for celecoxib suspension, 28 minutes for ibuprofen capsule, 40 minutes for celecoxib capsule, and >24 hours for placebo.

The results of the study reported in this Example clearly demonstrate that where rapid absorption of celecoxib, consistent with the pharmacokinetic profile described herein, can be obtained through formulation modification, surprisingly fast onset of analgesia is possible with this drug, equaling or even surpassing that obtainable with a standard formulation of ibuprofen.

Example 2

A celecoxib solution formulation, sf-1, was prepared having the composition shown in table 2.

TABLE 2

Composition (mg/g) of celecoxib solution formulation SF-1

| Component | SF-1 |
| --- | --- |
| Celecoxib | 200 |
| Water USP | 26 |
| HPMC (E5) | 38 |
| Ethanol | 113 |
| PEG 400 | 271 |
| PVP | 47 |
| Polysorbate 80 | 217 |
| Tromethamine | 26 |
| Oleic acid | 61 |
| Propyl gallate NF | 1 |
| Total | 1000 |

One gram of formulation SF-1 was individually placed into each of several hard gelatin capsules (Capsugel) to form Test Composition 1.

A celecoxib suspension for comparative purposes was prepared as follows:

A. Tween™ 80, 5.0 g, was placed in a volumetric flask.

B. Ethanol was added (to 100 ml) to form a mixture and the mixture was swirled to form a uniform solution.

C. A 5 ml aliquot of the uniform solution was transferred to a fresh 100 ml bottle containing 200 mg celecoxib, to form a premix.

D. Apple juice, 75 ml, was added to the premix to form an intermediate celecoxib suspension.

E. The intermediate celecoxib suspension was left to stand for 5 minutes, and was then shaken to form a celecoxib suspension for comparative purposes.

Figure 4:
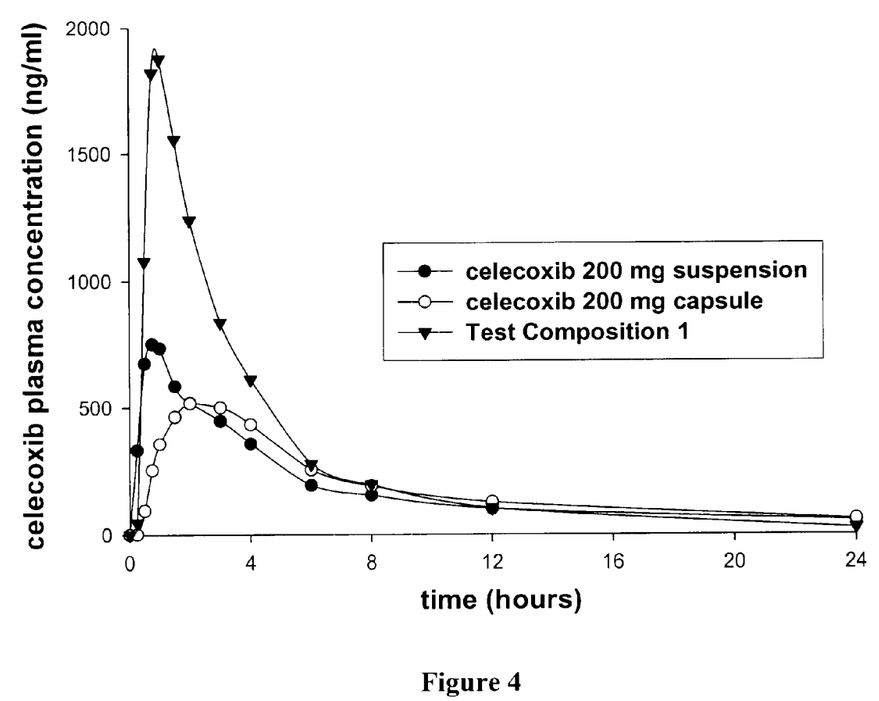
FIG. 4 shows blood plasma concentration profiles of celecoxib administered as a single oral dose of 200 mg, in the form of a capsule (Celebrex® 200 mg, Pharmacia Corporation), in the form of a suspension in apple juice as described in Example 2, or in the form of Test Composition 1 of Example 2.

Bioavailability parameters resulting from administration of Test Composition 1, in comparison with the above-described comparative celecoxib suspension and with a commercial celecoxib (Celebrex® of Pharmacia) 200 mg capsule, to human subjects were evaluated in a 24-subject, randomized, four period, balanced, crossover study. Study duration was approximately 15 days and subjects were randomly given one of each of the four dosage forms on days 1, 5, 9 and 12; administration of each dose was preceded by an 8 hour fasting period and was accompanied by 180 ml of water. Plasma blood levels for each subject were measured at pre-dose and at 15, 30, 45 minutes and 1, 1.5, 2, 3, 4, 6, 8, 12 and 24 hours after dosage administration. $C_{max}$ and AUC were calculated from the data in accordance with standard procedure in the art. As shown in FIG. 4, ingestion of Test Composition 1 resulted in a $C_{max}$ more than 2.5 times greater than resulted from ingestion of the comparative celecoxib suspension or the commercial celecoxib capsule. Ingestion of Test Composition 1 also resulted in an AUC 43% greater than, and a $T_{max}$ substantially similar to, that resulting from ingestion of the comparative celecoxib suspension.

Example 3

Two celecoxib/caffeine suspensions were prepared by the process described below.

1. PVP (K30) was added to water to form a PVP solution of 11.25 mg PVP/ml solution; 12 ml of the PVP solution were drawn in duplicate and placed into each of two vessels (A and B).

2. A 180 mg aliquot of caffeine was added to vessel A and a 900 mg aliquot of caffeine was added to vessel B to form caffeine suspensions A and B, respectively; both caffeine suspensions were sonicated as necessary.

3. A celecoxib suspension (in water) was prepared comprising 30% celecoxib and PVP (K30) at a concentration of 11.25 mg PVP/ml solution; the celecoxib suspension was wet milled using a Dynomill to form a milled celecoxib suspension.

4. Six ml of the milled celecoxib suspension were drawn in duplicate and were individually added to each of caffeine suspensions A and B to form celecoxib/caffeine suspensions A and B, respectively.

Example 4

Two solid celecoxib/caffeine compositions were prepared by the process described below.

1. Fifteen ml each of celecoxib/caffeine suspension A and B of Example 3 were drawn and placed into separate empty vessels.

2. Lactose (1.5 g) and 15 mg of sodium lauryl sulfate were added to each vessel with stirring to form intermediate suspensions A and B, respectively.

3. Intermediate suspensions A and B were individually spray dried using an apparatus consisting of an airbrush spray gun with an atomizing-air supply system set at 10 PSI, according to the following procedure.

(a) The spray gun was positioned approximately six inches from a glass plate.

(b) Heated dry air (from a heat gun) was supplied to the surface of the glass plate to obtain a resulting plate temperature of about 39–41° C.

(c) Fifteen ml of an intermediate suspension was delivered to the spray gun at a rate of 0.4–1.0 g/minute using a constant flow syringe pump;

(d) Solid celecoxib/caffeine composition was collected on the glass plate and was then removed with a single edged razor blade and collected in a vial.

Example 5

Two celecoxib/caffeine suspensions were prepared by the process described below.

1. PVP (K30) was added to water to form a PVP solution of 11.25 mg PVP/ml solution; 12 ml of the PVP solution were drawn in duplicate and placed into each of two vessels (A and B).

2. A 180 mg aliquot of caffeine was added to vessel A and a 900 mg aliquot of caffeine was added to vessel B to form caffeine suspensions A and B, respectively; both caffeine suspensions were sonicated as necessary.

3. A celecoxib suspension (in water) was prepared comprising 30% celecoxib and PVP (K30) at a concentration of 11.25 mg PVP/ml solution; the celecoxib suspension was wet milled using a Dynomill to form a milled celecoxib suspension.

4. Six ml of the milled celecoxib suspension were drawn in duplicate and were individually added to each of caffeine suspensions A and B to form celecoxib/caffeine suspensions A and B, respectively.

Example 6

Two solid celecoxib/caffeine compositions were prepared by the process described below.

1. Fifteen ml each of celecoxib/caffeine suspension A and B of Example 5 were drawn and placed into separate empty vessels.

2. Lactose (1.5 g) and 15 mg of sodium lauryl sulfate were added to each vessel with stirring to form intermediate suspensions A and B, respectively.

3. Intermediate suspensions A and B were individually spray dried using an apparatus consisting of an airbrush spray gun with an atomizing-air supply system set at 10 PSI, according to the following procedure.

(a) The spray gun was positioned approximately six inches from a glass plate.

(b) Heated dry air (from a heat gun) was supplied to the surface of the glass plate to obtain a resulting plate temperature of about 39–41° C.

(c) Fifteen ml of an intermediate suspension was delivered to the spray gun at a rate of 0.4–1.0 g/minute using a constant flow syringe pump;

(d) Solid celecoxib/caffeine composition was collected on the glass plate and was then removed with a single edged razor blade and collected in a vial.

What is claimed is:

1. A method for providing detectable pain relief within 30 minutes of administration in a mammalian subject in need thereof, the method comprising orally administering to the subject, a composition comprising celecoxib in a formulation which produces an effective pain-relieving concentration of at least about 250 ng/ml not later than about 30 minutes after oral administration.

2. The method of claim 1 wherein the composition is administered in an amount providing about 50 to about 400 celecoxib.

3. The method of claim 1 wherein the composition is administered in an amount providing about 100 to about 275 mg celecoxib.

4. The method of claim 1 wherein the mammalian subject is a human subject.

5. The method of claim 1 wherein a plasma concentration of celecoxib of at least about 300 ng/ml is attained not later than about 30 minutes after oral administration.

6. The method of claim 1 wherein a plasma concentration of celecoxib of at least about 400 ng/ml is attained not later than about 30 minutes after oral administration.

7. The method of claim 1 wherein a plasma concentration of celecoxib of at least about 250 ng/ml is attained not later than about 15 minutes after oral administration.

8. The method of claim 1 wherein a plasma concentration of celecoxib of at least about 300 ng/ml is attained not later than about 15 minutes after oral administration.

9. The method of claim 1 wherein the formulation produces a $T_{max}$ not greater than about 1.25 hours.

10. The method of claim 1 wherein the formulation produces a $T_{max}$ not greater than about 1 hour.

11. The method of claim 1 wherein the formulation produces a $T_{max}$ not greater than about 50% of the $T_{max}$ exhibited by a standard commercial formulation of celecoxib.

12. The method of claim 1 wherein the formulation produces a $T_{max}$ not greater than about 33% of the $T_{max}$ exhibited by a standard commercial formulation of celecoxib.

13. The method of claim 12 wherein the formulation produces a $T_{max}$ not greater than about 25% of the $T_{max}$ exhibited by a standard commercial formulation of celecoxib.

14. The method of claim 1 wherein the celecoxib is formulated as an ultra-fine dispersion or solution in a liquid medium.

15. The method of claim 1 wherein the celecoxib is formulated by dissolving the celecoxib in a suitable solvent and adding the resulting solution to an aqueous liquid to form a fine suspension, and wherein the suspension is administered to the subject not more than about 15 minutes after preparation.

16. The method of claim 1 wherein the celecoxib is in solution in a pharmaceutically acceptable solvent.

17. The method of claim 16 wherein the solvent is polyethylene glycol.

18. The method of claim 16 wherein the celecoxib formulation is encapsulated as a unit dosage form having a capsule wall.

19. The method of claim 18 wherein the wall comprises gelatin.

20. The method of claim 18 wherein the wall comprises hydroxypropylmethylcellulose.

21. The method of claim 1 that further comprises combination therapy with one or more drugs selected from opioids and other analgesics.

22. The method of claim 1 that further comprises combination therapy with an opioid compound selected from codeine, meperidine, and morphine or a derivative thereof.

23. The method of claim 1 wherein the subject suffers from headache or migraine and wherein there is further orally administered to the subject a vasomodulator, the celecoxib composition and the vasomodulator being administered in total and relative amounts effective to relieve pain in the headache or migraine.

24. The method of claim 23 wherein the vasomodulator is coformulated with the celecoxib composition.

25. The method of claim 1 wherein the subject suffers from headache or migraine and wherein there is further orally administered to the subject an alkylxanthine compound, the celecoxib composition and the alkylxanthine compound being administered in total and relative amounts effective to relieve pain in the headache or migraine.

26. The method of claim 25 wherein the alkylxanthine compound is coformulated with the celecoxib composition.

27. The method of claim 25 wherein the alkylxanthine compound is selected from caffeine, theophylline and theobromine.

28. The method of claim 27 wherein the alkylxanthine compound is caffeine.

29. The method of claim 1 wherein the celecoxib formulation provides detectable pain relief not later than about 15 minutes after oral administration.

* * * * *